United States Patent [19]

Kruy

[11] 4,207,873
[45] Jun. 17, 1980

[54] ENDOSCOPE DEFLECTION CONTROL

[75] Inventor: Theodore A. Kruy, Weston, Conn.

[73] Assignee: American Cystoscope Makers, Inc., Stamford, Conn.

[21] Appl. No.: 797,413

[22] Filed: May 16, 1977

[51] Int. Cl.² .............................................. A61B 1/00
[52] U.S. Cl. .................................. 128/6; 128/DIG. 9
[58] Field of Search ......................................... 128/4–8, 128/2 M, DIG. 9, 656, 657, 305.15; 74/528

[56] References Cited

U.S. PATENT DOCUMENTS 3,897,775  8/1975  Furihata ..................... 128/DIG. 9 X

FOREIGN PATENT DOCUMENTS 2328554  1/1974  Fed. Rep. of Germany .............. 128/6

Primary Examiner—Robert W. Michell
Assistant Examiner—Michael H. Thaler
Attorney, Agent, or Firm—St. Onge, Steward, Johnston, Reens & Noe

[57] ABSTRACT

An endoscope deflection control is described whereby enhanced one-hand control of the tip of a polydirectionally deflectable endoscope is obtained. The deflection control is mounted external to the head of the endoscope in such manner that convenient single-hand manipulation of deflection control wheels mounted on the head provides tip deflection in either a freewheeling deflection mode or an incremental mode characterized by discrete stable incremental tip deflections. Single-hand operation of the endoscope deflection control is obtained by locating incremental deflection position elements in a compact structure which is wholly or partly external to the head while the control wheels remain within manipulatable reach of the single hand's fingers. The deflection control wheels are under continuous control by the operator whose single hand may rotate either or both wheels in either mode and selectively, at any time, with the fingers of the same hand, may switch either or both control wheels into either of the modes by axially sliding the wheels into or out of engagement with associated incremental deflection position elements.

19 Claims, 5 Drawing Figures

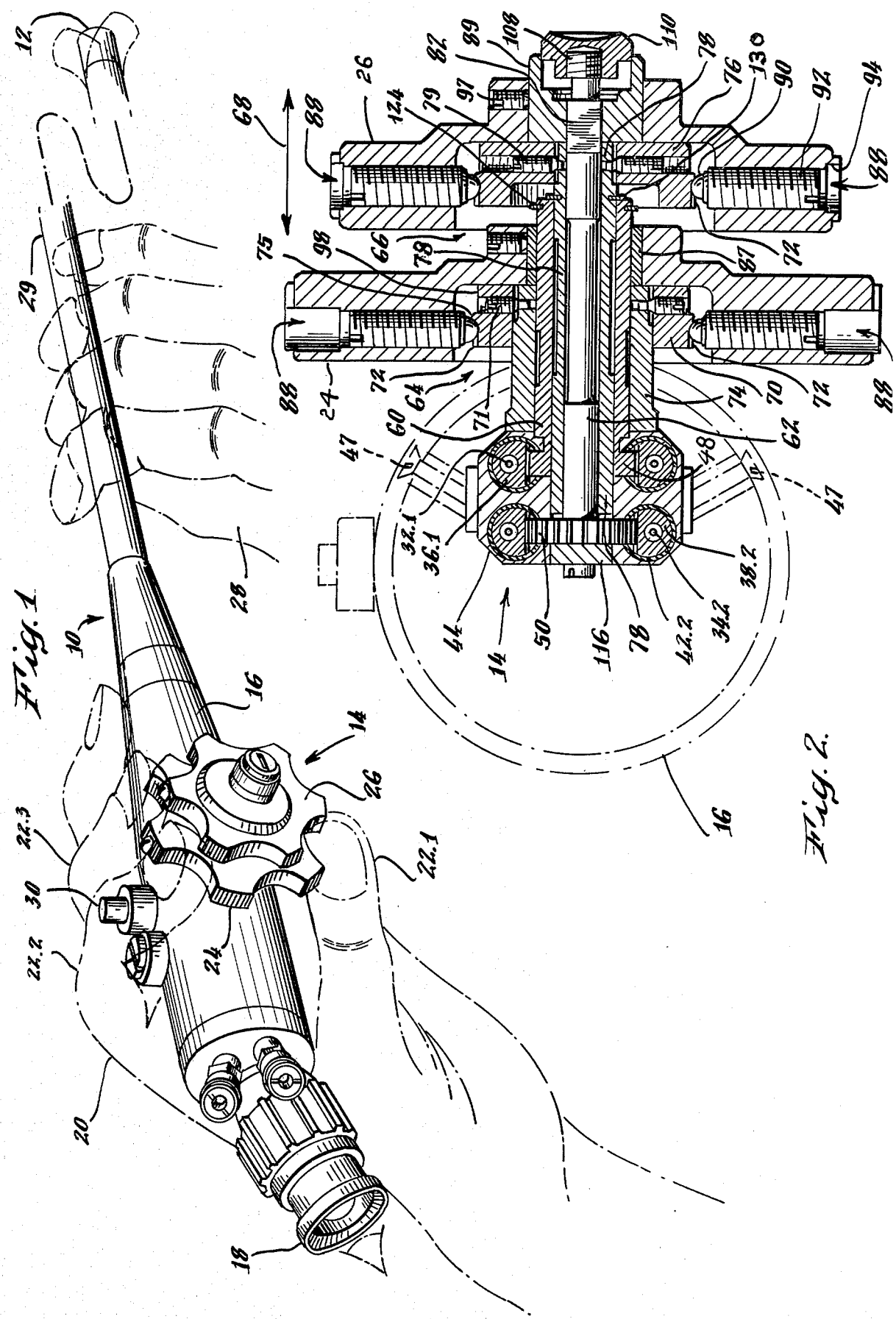

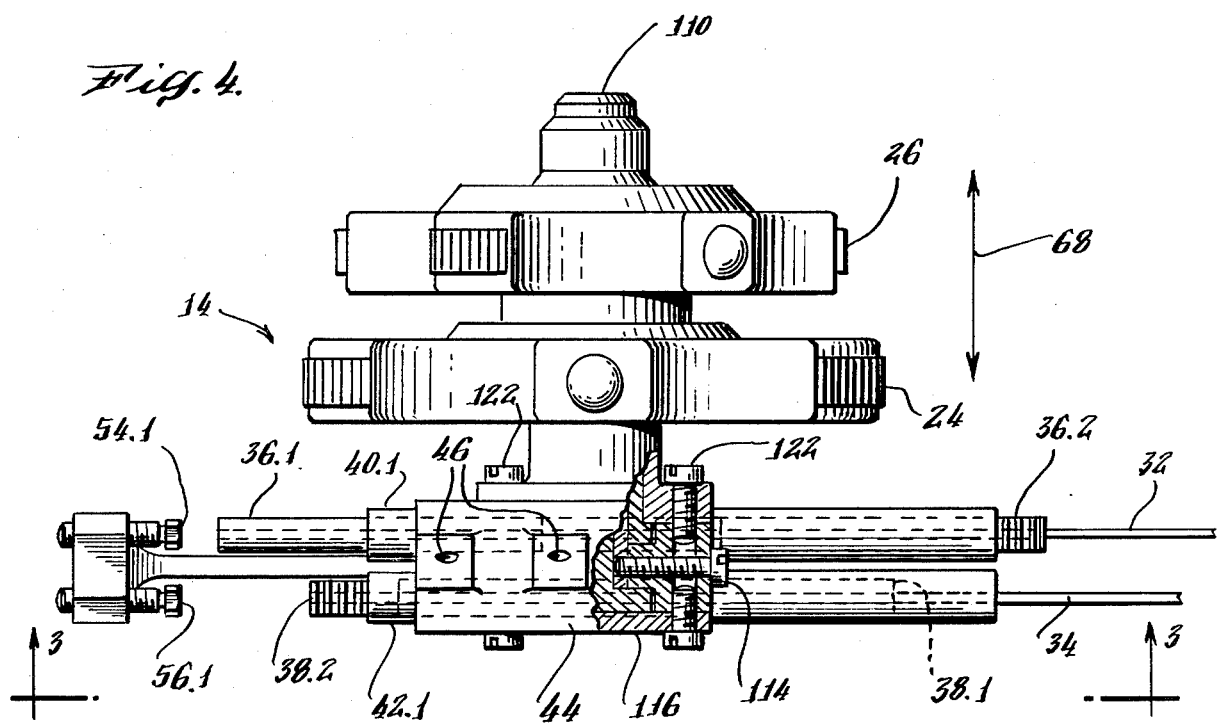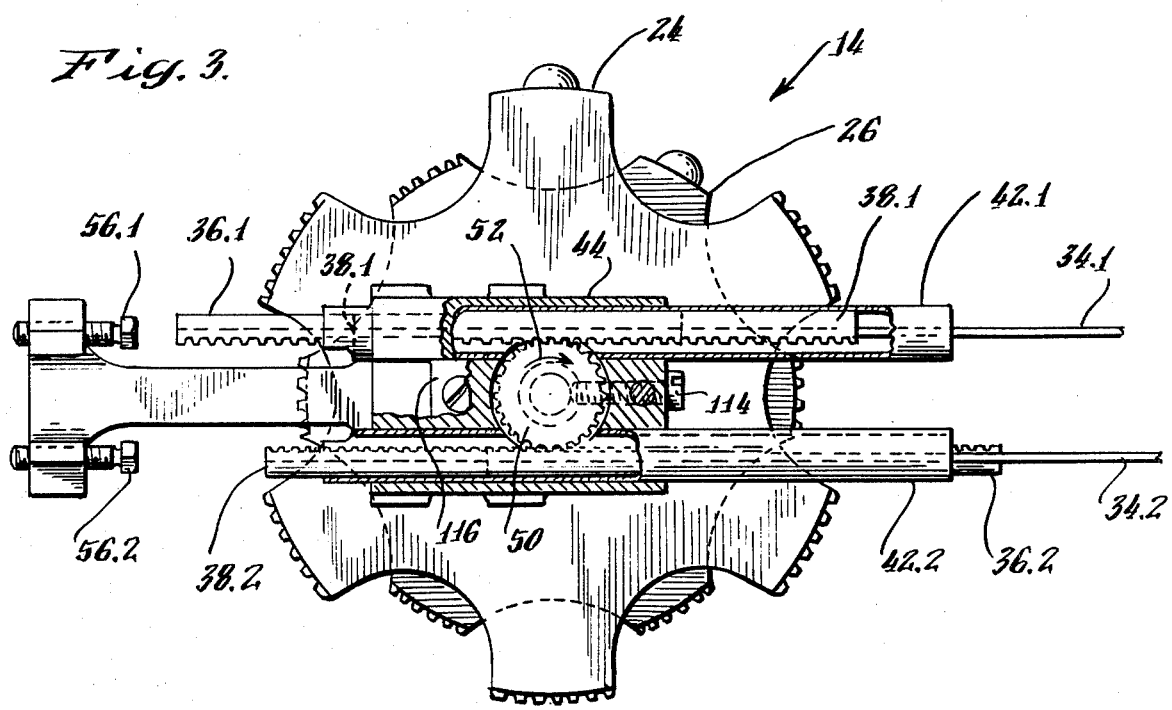

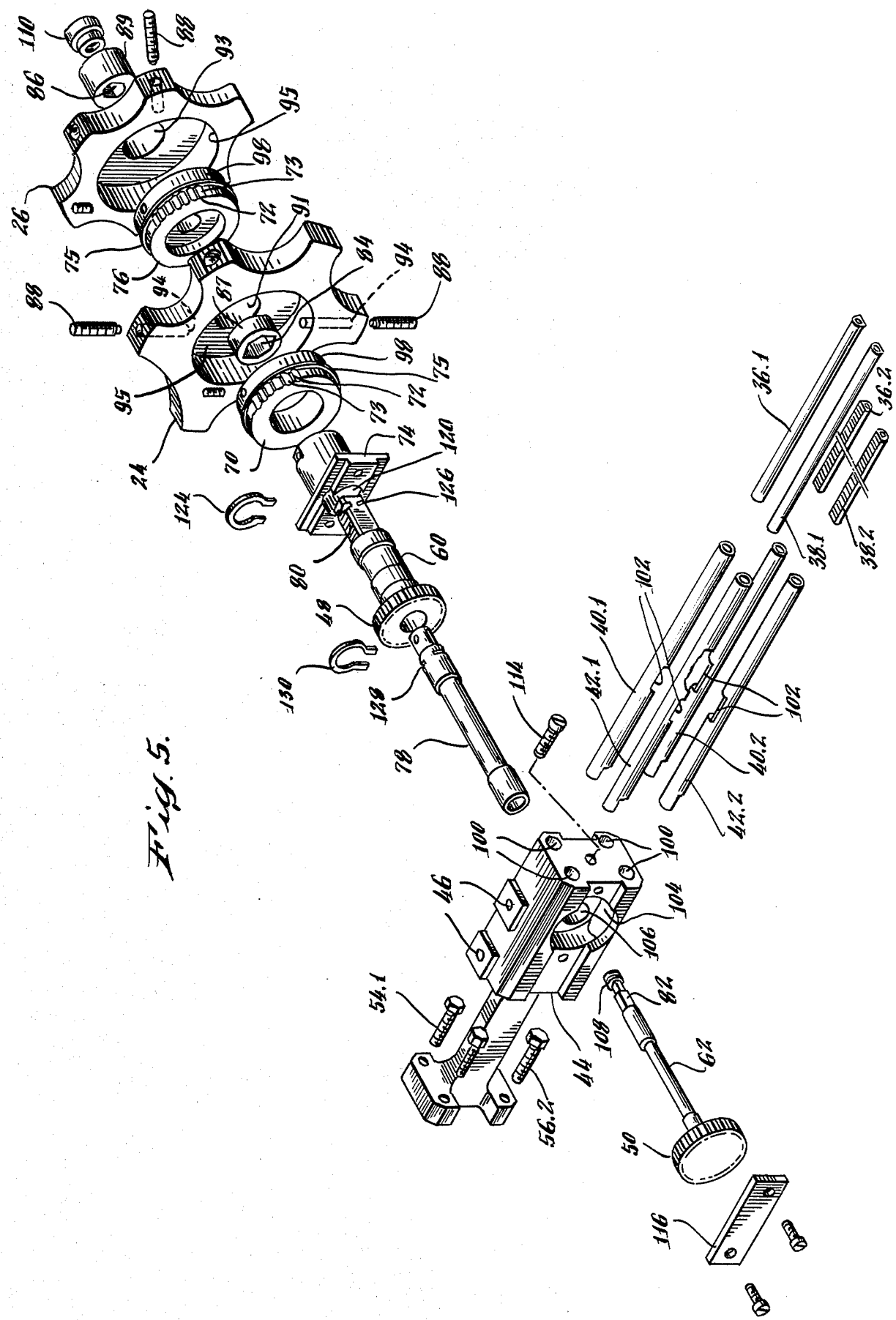

ENDOSCOPE DEFLECTION CONTROL

FIELD OF THE INVENTION

This invention relates to flexible endoscopes. More specifically, this invention relates to a deflection control to obtain polydirectional movement of the distal end of a flexible endoscope.

BACKGROUND OF THE INVENTION

Endoscopes are well-known optical imaging devices used for viewing objects within cavities or the internal surfaces of cavities, with additional capabilities of providing channels for insertion of devices to act upon or treat conditions of interest found. While the herein described invention has application in many fields, it has particular relevance to the medical field wherein flexible endoscopes are employed to view and treat deep and convoluted passages of the human body. In a typical endoscope designed for such purposes, the distal tip of the instrument is made maneuverable by employing four 90° spaced quadrant cables which interact mechanically with a series of vertebrated or specifically profiled rings located adjacent to the distal end of the instrument. Bending and deflection of the rings is obtained by tensioning and relaxing the cables in accordance with controls located at the proximal end of the fiberscope on the control head. The means for applying tensioning and relaxing forces to these quadrant cables have been the subject of extensive technological effort resulting in controls such as joysticks or coaxial control wheels found on many well-known fiberscopes. The object of these efforts has been to provide on the control head of the endoscope cable tensioning and relaxing means accessible and comfortable to the hands and fingers, and, consistent with holding the scope, operating all other controls, and allowing such other manipulations of the endoscope (i.e., torque, pushing and pulling) as are deemed effective for the clinical procedure for which the endoscope was designed.

The prior art control mechanisms for the deflection of the distal end of endoscopes are designed for access partially by one hand or both hands of the operator manipulating the proximal head of the instrument. The method of control acts upon the four control cables in two pairs, treating as a pair two control cables which are spaced 180° apart at a location of interaction with the aforementioned rings of the deflection system.

The prior art of more specific relevance to the invention herein discussed consists of designs embodying two coaxial control wheels mounted externally to the proximal control housing of the endoscope. The turning of one wheel at the head of the instrument acts to tension one cable of a pair of control cables while simultaneously releasing tension on the other cable in that pair of cables. The turning of the other control wheel acts similarly upon the other pair of control cables. The two wheels may be operated simultaneously.

As an aid in fixing the deflected distal endoscope section in a particular desired oposition, the deflection controls at the head of the instrument have included means to fix the control wheels in a particular position. One prior art means to accomplish this includes friction devices applied such as to place drag on the control wheels. For example, an operator wishing to place drag on the deflection control wheels actuates a lever or other device controlling the drag. Light drag or heavy drag results from the position selected for the drag control lever.

If some intermediate drag is desired, an intermediate position of the drag adjusting lever is selected. A specific desired or useful amount of drag can be determined only by trial and error involving setting of the drag control lever, turning the control wheels, resetting the lever closer to the optimum setting, again trying the wheels, etc. The same time-consuming exercise is required for the second wheel, and if the free running position is reestablished for any reason, the whole trial and error process must be repeated when next a drag mode is desired. In practice, this procedure results in acceptance of the initial setting of the drag control lever and attempting to work under less than optimum conditions.

Another prior art drag control applies a fixed amount of friction drag upon actuation of a control device. A disadvantage of prior art drag systems for endoscope deflection devices, which apply a friction effect either adjustably or fixedly, is an inability to achieve precise and predictable incremental movements of the deflection control. When pressure to turn a control wheel is applied, the drag is suddenly overcome, the wheel turns and, upon conscious release of turning pressure, the wheel stops turning and the instrument tip stops deflecting at a position sometimes not far enough, sometimes too far, sometimes just right, but generally at an imprecise and unpredictable position. This tendency to overshoot or undershoot a desired position calls for time-consuming maneuvers or alternatively calls for the use of both hands in attempting to minimize the over-undershoot effect.

Another disadvantage of prior art control wheel drag designs for deflection of control wheels is the negative effect on the degree to which the proximal deflection controls of the endoscope can be controlled with one hand. Ideally, the left hand holds and controls the proximal control head of the endoscope while the right hand is on the flexible insertion tube of the instrument controlling pushing and pulling and applying left or right torque to the shaft end of the endoscope.

The prior art drag designs require that the right hand be used far more often to achieve and hold the exact deflection position than is desirable. As a result, the right hand must move quickly to and from the shaft of the endoscope to again hold the desired next deflecting position and the next and the next in a series of repeated movements tending to interfere with the smooth progress of the insertion of the instrument into the body cavity. If the right hand is required to achieve each of these precise solutions, its function on the flexible shaft of the scope is continually interrupted. Removing the right hand from the flexible shaft often loses a desired tip position and time is lost in recovering that position.

In another prior art endoscope of substantially smaller size, specifically a bronchoscope having deflection in one plane only and incorporating only one pair of tensioning and relaxing cables, a toothed wheel inside the control housing interacts with a spring member to provide deflection increments. In attempting to adapt this construction to much larger endoscopes having more than one deflection wheel for polydirectional control, it was found that the space and strength requirements of the larger scope were such as to preclude adaptions of such control inside the control head of the endoscope. This is particularly so when each deflection control wheel is to be capable of providing either continuous mode deflection or incremental mode deflection and further when such selection is to be exercisable with a single hand. It became evident that a further disadvantage of an interior mounted incrementing and mode selection mechanism resides in the need to disassemble the endoscope whenever the mechanism needs adjustment.

In summary, the prior art approach to apply friction drag to the deflection control wheels of an endoscope deflection control generally encounters four main deficiencies:

(1) The setting of the desired amount of drag is imprecise and requires time with trial and error settings;
(2) the drag system tends to be imprecise and unpredictable and positioning the endoscope distal tip because of the tendency to over or undershoot its next position;
(3) the right hand is needed to minimize the foregoing negative effects and is, therefore, forced continually to be removed from its preferred flexibleshaft-holding location. As a result there is a general loss in hand-eye coordination in applying the endoscope instrument as it is employed through difficult intubation maneuvers;
(4) the crowded interior and strength required of the control heads for large endoscopes inhibits the internal placement of devices for overcoming these deficiencies.

SUMMARY OF THE INVENTION

In a flexible endoscope deflection control in accordance with the invention, the control head of the instrument is shaped and sized to be held by one hand while the deflection controls are so located as to be manipulatable by the fingers of the same hand. The deflection controls are also conveniently manipulated by the same hand to provide either continuous smooth control over the deflection of the distal end of the endoscope or by a simple adjustment apply drag in the form of discrete incremental positional detents over each deflection. The means for deflection control, and the means of selecting one mode or the other, are external to the proximal housing to prevent undesirable increase in the size of the control head to the point of being uncomfortable in the hand, while preserving easy access for adjustments such as selection of the mobility of the wheels between their incremental mode positions.

With a mechanism for applying the deflection control in accordance with the invention, the same hand can entirely control the instrument for deflection while placing a sufficient amount of drag on the control to hold the endoscope distal end in any desired deflection position. Small precisely predictable amounts of motion may be applied to the deflecting distal tip without overshooting or undershooting a desired position. With the mechanism for endoscope deflection in accordance with the invention, the hand not engaged in holding and controlling the control head of the endoscope may be freed to an optimum extent for the control of the flexible insertion shaft of the instrument to achieve enhanced control and ease of manipulation.

In one form of an endoscope deflection control in accordance with the invention, a pair of coaxially mounted control wheels are located on the head of the instrument. The instrument head is sized and shaped so that one hand may conveniently grip it while the wheels are located within finger-reaching distance for control over the deflection of the distal end of the instrument.

The wheels are so positioned as to be each axially movable by the fingers of the hand gripping the instrument head between a free-wheeling mode with no drag and a drag mode in which the wheel is limited to specific incremental rotational positions. Each incremental position is selectively spaced such as equi-distant from the other in terms of angular rotation and sufficiently secure to be able to retain the tip deflection at this position.

The deflection wheels are mounted on a side of the head of the endoscope within finger control of the single hand used to manipulate the head. The deflection control includes incremental positioning devices which are mounted external of the normally employed head in a compact structure to preserve the single hand control. The external mounting facilititates adaption of the endoscope head so that the incremental positioning devices may be added with reduced design disturbance of the head shape. In this manner access for necessary adjustments such as the stability of each wheel in an incremental position can be made to suit the operator or compensate for wear and the like.

A particular advantage of the deflection control in accordance with the invention resides in the ability to establish either of the operational modes without requiring the use of the other hand. In this manner the free hand can be left to accomplish its major task of manipulating the shaft of the endoscope for its advancement, retraction, or left and right torque, within the body cavity. It is not here suggested that the present invention succeeds in fully establishing complete one-hand operator control of all the maneuvers required of flexible endoscopes, but it is claimed that an operator can develop a substantially higher degree of single-hand deflection control in comparison with prior art adjustable drag designs.

It is, therefore, an object of the invention to provide an endoscope deflection control which is conveniently operated by a single hand while providing precise discrete endoscope deflection positions which are stable and easily achieved under single hand control.

These and other objects and advantages of an endoscope deflection control in accordance with the invention can be understood from the following preferred embodiment described in conjunction with the drawings.

BRIEF DESCRIPTION OF THE DRAWINGS

FIG. 1 is a perspective view, approximately to scale, of the head of a flexible endoscope showing its proximal end under control by the hand of an operator;

FIG. 2 is an enlarged section view of an endoscope deflection control employed for use in the head of the instrument shown in FIG. 1;

FIG. 3 is a side partially broken away view in elevation of the deflection control mechanism shown in FIG. 2;

FIG. 4 is a top partially broken away view of the deflection control mechanism shown in FIG. 2; and FIG. 5 is an exploded perspective view of components employed in the endoscope deflection control.

DETAILED DESCRIPTION OF EMBODIMENT

With reference to FIG. 1, a endoscope 10 is shown. The endoscope 10 includes a distal end 12 which may be maneuvered and deflected in a multiple of positions (such as shown in dotted lines) under control by a deflection mechanism 14 located and mounted externally to a side of a longitudinal head 16 of the endoscope 10.

the endoscope 10 is provided with suitable utility channels such as for observing through an optical fiber bundle to form a fiberscope, and to supply therapeutic treatment in a manner well known in the art of flexible endoscopes. In a typical use of a flexible fiberscope, the operator observes the internal body cavity through an eyepiece 18 while holding the head 16 of the instrument 10 usually in the left hand 20 with the fingers 22 in contact with deflection control wheels 24, 26. Commonly the thumb 22.1 is located below the head 16 to engage the bottom part of either wheels 24 or 26 while the forefinger 22.2 and middle finger 22.3 engage the upper parts of either one of wheels 24, 26. The right hand 28 is employed on the flexible shaft segment 29 of the endoscope 10 to control its advancement through the body cavity.

In the head 16 deflection control is obtained with rotationally mounted control wheels 24, 26 located within reach of the left hand fingers 22. As a result, the head 16 is sized and shaped so that the left hand 20 can enclose it and firmly grip it while simultaneously contacting the deflection wheels 24, 26 for maneuvering of distal end 12. The inclusion of the deflection mechanism 14 as shown in FIG. 1 has preserved the convenient left-hand grippability of the head 16 of endoscope 10 while maintaining finger control over the rotation of deflection wheels 24, 26.

The term "wheels" as employed herein is intended to include other actuating elements such as a lever capable of providing the desired distal end deflection in response to single hand control.

The control wheels 24, 26 may be axially moved towards and away from head 16 between two modes. In one mode, for example, when pulled close to the head 16, the wheels 24, 26 will engage an incrementing mechanism which provides discrete incremental rotational positions. In this manner the operator may move the distal end 12 and deflect it a precise small amount for each incremental change and the deflected distal end will retain the new position.

In another mode the operator may desire to deflect the distal end 12 in a continuous manner and to achieve such control pushes the appropriate wheel away from the head 16 to a freewheeling position.

In the illustrated embodiment the wheel 24 nearest the head 16 of instrument 10 is larger than the wheel 26. The size of head 16 permits one to controllably engage both the near and far wheels 24, 26. However, as will be further explained, the wheels 24, 26 may be interchanged whereby the smaller is on the inside and the larger on the outside. Other instrument controls are provided within convenient reach of the single hand fingers 22.2 or 22.3 by locating pushbutton 30 as indicated in FIG. 1 to, for example, supply when actuated liquid to clean the viewing end of the endoscope.

With reference to FIGS. 2, 3 and 4, the endoscope deflection mechanism 14 is shown coupled to two pairs of cables 32, 34 running down the length of the endoscope 10 to control rings or vertebrae for deflection of the distal end 12. The cables 32, 34 are generally arranged in a rectangular pattern with deflection control exercised in each pair by tensioning one cable while relaxing the other. Details for the cable deflection system are well known and need not be further described.

In the endoscope deflection control 14 depicted in the figures, the cables 32, 34 are each attached to truncated cylindrical racks 36, 38 mounted in cylindrical guides 40, 42 attached to and held within a yoke body 44. The yoke body 44 is provided with suitable mounting holes 46 for attachment within the head 16 of the endoscope instrument 10 such as with flat head screws 47. The racks 36, 38 are engaged by pinions 48, 50 respectively engaging racks 36.1-36.2 and 38.1-38.2 at diametrically opposite locations (see FIG. 3). In this manner rotation of a pinion, for example 50, in a clockwise direction indicated by arrow 52 in FIG. 3, causes movement away from a yoke stop 56.1 by rack 38.1 and advancement toward yoke stop 56.2 of the other rack 38.2 to correspondingly relax cable 34.1 while tensioning cable 34.2.

Each pinion 48, 50 is connected to a shaft, such as an outer shaft 60 for the rear located rack drive pinion 48 and an inner shaft 62 for the front rack drive pinion 50. The shafts, 60, 62 are coaxially located and laterally extend from the yoke body 44 for engagement with control wheels 24, 26 respectively.

Releasable incremental rotational positioning devices 64, 66 are provided and mounted so that wheels 24, 26 may be axially moved in the direction of arrow 68 into either engagement with or release from an associated incrementing device 64, 66. The incremental devices 64, 66 as shown in FIG. 2 are mounted in counterbored recesses of the wheels so as to fit in general coplanar relationship with the wheels.

As illustrated in FIG. 2, the wheel 24 adjacent head 16 is operatively disposed with respect to a ratchet 70 in the form of a hub carrying serrations 72. Ratchet 70 is mounted with set screws 71 on a support 74 laterally extending from and connected to the yoke body 44. In a similar manner a ratchet 76 in the form of a serrated hub is mounted with set screws 79 to a center shaft 78 located to laterally extend between the outer and inner shafts 60, 62 and affixed to the yoke body 44.

The outer and inner shafts 60, 62 are respectively provided with keyed ends 80, 82, such as a hexagonal crosssection for end 80 and square for end 82 (see FIG. 5), for engagement with similarly shaped apertures 84, 86 in bushings 87, 89 mounted in bores 91, 93 of wheels 24, 26.

The control wheels 24, 26 are interchangeable by sizing their through bores 91, 93 and counterbore 95 to be equal. The bores 91, 93 respectively removably receive bushings 87, 89 held to the wheels with set screws such as 97. Each wheel counterbore 95 is sized to freely receive a ratchet 70 or 76 as shown in FIG. 2. The key-shaped through bore 84 of bushing 87 slidingly meshes with the corresponding key-shaped segment 80 of outer shaft 60. In a similar manner key-shaped through bore 86 of bushing 89 slidingly meshes with the keyed segment 82 of inner shaft 62 while the entire bushing 89 fits inside the control wheel's 26 through bore 93 which is the same size as through bore 91. In this manner the wheels 24, 26 can be axially movable while maintaining rotational control over shafts 60, 62.

Radially adjustable pairs of pawls 88 are mounted in each wheel to positively seat between serrations 72 for precise rotational detent positions. Each pawl 88 is formed with a spring loaded ball 90 seated with a set screw 92 in a hole 94 extending into a counterbore 95 of a wheel. The contact force of a pawl 88 with a ratchet can be selected by control over the pawl's position within the radially threaded hole 94.

The advantage of employing imcrement positioning devices 64, 66 external of head 16 can be appreciated when adjustments are to be made to select the contact force. For example, the force may be adjusted to suit the requirements of a particular operator or to compensate for wear in the serrations. These force adjustments vary the ease of mobility of the wheels 24, 26 and are conveniently implemented without requiring disassembly of parts.

Each serration 72 is formed in such manner that between each other are stable detent positions for each wheel 24 or 26. The spacing 73 between the serrations 72 are further designed to terminate short of the axial end of the ratchets to leave a slight lip 75 over which each pawl 88 must be urged. The resulting change from one free-wheeling mode to an incremental positioning mode is thus obtained with a positive snap-like action for improved operator single-hand control.

In the operation of the deflection control 14, the fingers 22 of the left hand, for example, may rotate the front wheel 24 and move it to either one of its axial positions. When moved close to head 16 or yoke 44, the pawls 88 in knob 24 are moved from above a radially recessed shoulder 98 on ratchet 70 into contact with a detent position between serrations 72 of ratchet 70. As wheel 24, thereafter, may be rotated to deflect distal end 12 of endoscope 10, each detent position of pawls 88 present precise rotational increments with sufficient stability to maintain the desired distal end deflection.

The number of serrations or detent positions 72 on a ratchet determines the number of specific positions the deflection system may assume. If normal use requires precise control and small tip deflections, a large number of serrations is selected. Generally, the number of serrations on a ratchet 70 or 76 is selected sufficiently high so that each incremental wheel rotation involves deflections which are sufficiently small to provide high resolution deflection control over the distal end 12. A practical number of incremental positions may be such that each provides for about four to nine degrees of deflection of distal end 12. However, greater resolution can be achieved by increasing the number of serrations so that the angular deflection between successive serrations is in very small, stable increments.

The form of the serrations 72 and the radial spacing between surface 98 of each ratchet are so selected that lateral movement of a control wheel from a free-wheeling position, with pawls 92 over surface 98, to an incremental position with pawls 92 into contact with serrations 72, is easily carried out under single-hand control.

In the embodiment wheels 24, 26 are shown of different sizes with effectively different control diameters. Hence, the turning force required for these wheels may differ, particularly since the hub shaped ratchets have the same effective diameter. The turning forces, however, may be conveniently adjusted by radially moving the pawls 88 so that the wheels 24, 26 may be easily moved from one detent position to another under singlehand control while each detent position is sufficiently stable to hold the distal end 12 in its deflected position.

As illustrated in FIG. 2, the deflection control 14 extends laterally from the outer shell of the head 16. This arrangement enables efficient use of the space within head 16 for such other devices and channels employed to provide well known endoscope functions. The incrementing devices 64, 66, when incorporated inside the housing 16, require extensive redesign and possibly undesirable rearrangement of components inside the housing. The external location of incrementing devices 64, 66 hence enables a reliable deflection control which can be conveniently adjusted to fit individual needs.

The term "external" as employed here with respect to the mounting of the deflection control and its incrementing devices is relative to the head 16. It should be understood, however, that variations in the shape of the head 16 may be contemplated to give an appearance of including the incrementing devices 64, 66 inside the head 16. The term "external" as used herein thus should be construed to include those side-located arrangements of incrementing devices which can be conveniently accessed for adjustment and maintenance without impairing the single-hand control characteristics of the flexible endoscope 10.

As illustrated for further detail in the perspective and exploded view of FIG. 5, the yoke body 44 includes guide bores 100 sized to receive guides 40, 42 with a tight clamping fit. The rack guides 40, 42 are cut out at sections 102 for location opposite a counter bore 104 of yoke body 44 where the rack drive pinions 48, 50 are to be mounted for engagement with racks 36, 38 slidingly mounted in the guides.

The inner shaft 62 is connected to the front rack drive pinion 50 and extends laterally through bore 106 in the yoke body 44 with a threaded segment 108 at end 82 to receive a nut 110 which also serves as an axial stop for the rear control wheel 26.

The inner shaft 62 is mounted for rotation within center shaft 78 which is affixed within a bore 112 of yoke body 44 with an antirotation set screw 114 to laterally extend from the yoke body 44. The center shaft 78 terminates near the keyed segment 82 of the inner shaft 62 to allow attachment of wheel 26 while the ratchet 76 is affixed as shown in FIG. 2. A rear cover plate 116 is provided to capture pinion 50 in counter bore 104.

The fixed center shaft 78 in turn fits inside the outer shaft 60 which is connected to rack drive pinion 48 located in a similar counter bore as 104 but on the other side of the yoke body 40. The outer shaft 60 rotates with its key-shaped segment 80 engaging the front located wheel 24. The outer shaft 60 in turn fits within the through bore 120 of support 74 affixed to the yoke body 44 with screws 122. The support 74 in turn provides a fixed mounting for the ratchet 72.

As illustrated more clearly in the views of FIGS. 2 and 5, the outer shaft 60 is provided near its end with a retainer ring 124 mounted in a suitable annular groove 126 to serve as an axial stop for the control wheel 24 while permitting shaft 60 to rotate. The center shaft 78 is provided with a groove 128 for receiving a retainer ring 130 to axially retain the outer shaft 60.

Having thus described an endoscope deflection control in accordance with the invention, its advantages can be appreciated. One hand of the operator can provide and precisely control the deflection of the distal end of the endoscope while the other hand can maintain its manipulative control of the flexible shaft of the instrument by pushing, pulling or torquing. The operator may conveniently change the mode of the deflection control from a continuously scanning deflection to a mode with discrete stable incremental positions whose increments are achieved with butter-smooth control.

The invention has been described with a preferred embodiment, variations of which may occur to one skilled in the art. For example, the coupling drive between the cables 32, 34 and the wheels is shown to incorporate pinions 48, 50 and racks 36, 38. Other coupling drives may be employed and which respond to the rotational movements of control wheels 24, 26. The ratchets and pawls may be reversed, in that the pawls are effectively mounted in a stationary position on the yoke body and the ratchets rotated by their mounting on the control wheels. The incrementing devices can be separated from the wheels and the lips 75 on the ratchets may be formed of separate washers to perform an equivalent function. Other variations may be contemplated within the scope of the invention as determined by the following claims.

What is claimed is:

1. A deflection control for a flexible endoscope having a control housing on its proximal end and a deflectable section at its distal end, with deflection operated by cable means extending from proximal to distal end and a manual deflection control means comprising
   a proximal control head shaped and sized for single-hand gripping and operation of controls placed thereon, said control head being provided on one side thereof and externally thereto with first and second deflection control wheels mounted for rotation to the control head;
   means for coupling said first and second control wheels to said deflection control cables for deflection of the distal end of the endoscope in response to wheel rotation;
   incrementing means located externally to the control housing for enabling uniform small incremental rotational motions of each of said first and second control wheels with stable fixed wheel positions between such incremental motions; and
   engaging means located external to the control housing for permitting each of said first and second control wheels to be moved independently of the other wheel into and out of engagement with said incrementing means while said control wheels remain coupled to said deflection cables by said coupling means, whereby continuous and incremental deflection control of the distal portion of the endoscope are individually and selectively obtainable for each of said control wheels.

2. The endoscope deflection control as claimed in claim 1 wherein the engaging means mounts said first and second control wheels for rotation about a common axis with movement along said axis for selective engagement with and release from said incrementing means.

3. A deflection control for a flexible endoscope having a distal end which can be deflected with deflection cables extending from the head at the proximal end of the endoscope to the distal end, comprising
   an endoscope deflection control head generally shaped and sized for single-hand manual gripping and control, said control head being provided on one side thereof and within finger distance control with first and second control wheels mounted for rotation to the deflection control head;
   means mounted to said control head for coupling the first and second control wheels to said deflection cables for deflection of the distal end of the endoscope in response to wheel rotation;
   incrementing means located external of said control head for establishing stable incremental wheel rotational positions for said first and second control wheels;
   means for mounting said first and second control wheels to be each movable independently of the other wheel under single-hand control for engagement and release with respect to said incrementing means while remaining coupled to the deflection cable by said coupling means, whereby deflection control of the endoscope distal end is selectably obtainable with either continuous wheel movement with or with incremental wheel rotation for each of said wheels under single hand control.

4. The endoscope deflection control as claimed in claim 3 wherein the mounting means enables the first and second control wheels to rotate about a common axis with predetermined axial movement for each wheel selected to control engagement and release with respect to the incrementing means.

5. The endoscope deflection control as claimed in claim 4 wherein the wheels are differently sized with the larger wheel located adjacent to the deflection control head.

6. The endoscope deflection control as claimed in claim 4 wherein said wheels are differently sized and removably mounted to said deflection control head, said wheels further being shaped to be interchangeable and enable selection of the desired position of the differently sized wheels.

7. The endoscope deflection control as claimed in claim 3 wherein the incrementing means is formed of first and second pairs of elements, each pair being formed of a hub carrying serrations and detent positions with the serrations separating the detent positions about the axis of rotation of said wheels and
   a pawl for operatively engaging detent positions between the serrations of a hub,
   one element in each pair being effectively connected to the deflection control head and the other element in each pair being connected to a wheel.

8. A deflection control for an endoscope having a distal end which can be deflected with deflection cables extending from the deflection control head at the proximal end of the endoscope to the distal end, comprising
   an endoscope deflection control head generally shaped and sized for single-hand manual gripping and control, said control head being provided on one side thereof and within finger distance control with first and second control wheels mounted for rotation to the head;
   an inner shaft and an outer shaft laterally extending from said head and respectively coupled to said first and second control wheels for rotational control thereby about an axis, means for mounting said first and second control wheels to be each axially movable on said shafts between first and second deflection mode positions while maintaining said rotational shaft control;
   means for coupling the inner and outer shafts to said deflection cables for deflection of the distal end of the endoscope in response to wheel rotation;
   incrementing means mounted externally to said control head and operatively axially disposed with respect to said first and second wheels for establishing stable incremental rotational positions for said wheels in said first axial deflection mode position thereof and being disengaged from said wheels to enable a free turning of the wheels in said second axial deflection mode position thereof;
   each of said first and second control wheels being individually rotatably and axially movable independently of the other wheel between their deflection mode positions under single-hand control for engagement and release with respect to said incrementing means while remaining coupled to the deflection cable by said coupling means, whereby deflection control of the endoscope distal end is selectably obtainable with either continuous wheel movement or with incremental wheel rotation under single-hand control.

9. The endoscope deflection control as claimed in claim 8 wherein said deflection head is further provided with a yoke body sized to fit within the head, said yoke body being provided with a central support shaft and an outer support laterally extending in coaxial relationship with each other and the inner and outer shafts, with said incrementing means effectively mounted on said central support shaft and said outer support to provide the stable incremental positions.

10. The endoscope deflection contol as claimed in claim 9 wherein said incrementing means includes pawls and ratchets, said ratchets having serrations separating detent positions, and
a lip effectively axially interposed between the detent position and the second deflection mode positions of the wheels to provide operator selectable axial separation between the first and second mode positions of the control wheels.

11. The endoscope deflection control as claimed in claim 10 wherein the lip is formed on each of the ratchets with each ratchet further being provided with a recessed annular shoulder to seat a pawl in the second deflection mode position of the control wheels.

12. The endoscope deflection control as claimed in claim 11 wherein said ratchets are mounted respectively on said central support shaft and said outer support and wherein said pawls are movably mounted on said control wheels.

13. The endoscope deflection control as claimed in claim 6 wherein said control wheels engage the inner and outer shafts in axially aligned keyed relationship to enable axial movement of the control wheels while maintaining rotational control over said inner and outer shafts.

14. A deflection control for an endoscope having a distal end which can be deflected with first and second pairs of deflection cables extending from a head at the proximal end of the endoscop to its distal end comprising
a yoke body sized to fit within the head of the endoscope;
first and second pairs of racks mounted for operative movement along a preselected direction to said yoke body, said first and second pairs of deflection cables being respectively connected to said first and second pairs of racks;
front and rear rack drive pinions each respectively in coupling engagement with a pair or racks for drive thereof along said operative direction in response to rack drive pinion rotation;
an inner shaft coupled to rotate the front rack drive pinion and extending laterally from the yoke body for manual rotation control;
an outer shaft mounted coaxially with the inner shaft and coupled to the rear rack drive pinion for rotation thereof, said outer shaft extending laterally from the yoke body and having a length selected to expose a laterally extending end of the inner shaft for its rotational control;
rear ratchet means affixed to the yoke body and located adjacent an end of the outer shaft for establishing incremental rotational positions for the outer shaft;
front ratchet means affixed to the yoke body and located adjacent the exposed lateral end of the inner shaft for establishing incremental rotational positions for the inner shaft;
rear wheel means slidably mounted to and in key relationship with the outer shaft for selective operative engagement and release with the rear ratchet means while retaining rotational drive control over the outer shaft; and
front wheel means slidably mounted to and in keyed relationship with the inner shaft for selective operative engagement and release with the front ratchet means while retaining rotational drive control over the inner shaft.

15. The deflection control for an endoscope as claimed in claim 14 wherein the front and rear ratchet means each include a raised surface which is axially disposed to separate a free-wheeling mode axial wheel position from a discrete rotational incremental mode axial wheel position.

16. The deflection control for an endoscope as claimed in claim 15 wherein the wheel means each include adjustable pawls oriented to engage a ratchet means.

17. The deflection control for an endoscope as claimed in claim 14 wherein each wheel means is further provided with removable bushings sized to respectively slidingly engage said inner and outer shafts, said bushings having like peripheral mounting surfaces to render said knob means interchangeable.

18. A deflection control for a flexible endoscope having a distal end which can be deflected with deflection cables extending from the deflection control head at the proximal end of the endoscope to the distal end, comprising
an endoscope deflection control head generally shaped and sized for single-hand manual gripping and control, said control head being provided on one external side thereof, and within finger distance control, with first and second control wheels mounted for rotation to the head;
means mounted to said control head for coupling the first and second control wheels to said deflection cables for deflection of the distal end of the endoscope in response to wheel rotation;
incrementing devices located in general coplanar relationship with said externally mounted control wheels to establish incremental wheel rotational positions for said first and second control wheels;
means for mounting said first and second control wheels to enable each of said control wheels to be individually movable independently of the other wheel under single-hand control for engagement and release with respect to said incrementing devices while remaining coupled to the deflection cable by said coupling means, whereby deflection control of the endoscope distal end is selectively obtainable with either continuous wheel movement or with incremental wheel rotation under single hand control.

19. The deflection control for a flexible endoscope as claimed in claim 18 wherein said first and second control wheels are provided with recesses sized and shaped to retain said incrementing devices in general coplanar relationship.

* * * * *